(12) United States Patent
Wong et al.

(10) Patent No.: US 11,160,468 B2
(45) Date of Patent: Nov. 2, 2021

(54) MRI-COMPATIBLE PATIENT SUPPORT SYSTEM

(71) Applicant: Profound Medical Inc., Mississauga (CA)

(72) Inventors: Ting Wong, Oakville (CA); Michael Wybenga, Hamilton (CA)

(73) Assignee: Profound Medical Inc., Mississauga (CA)

( * ) Notice: Subject to any disclaimer, the term of this patent is extended or adjusted under 35 U.S.C. 154(b) by 162 days.

(21) Appl. No.: 16/453,499

(22) Filed: Jun. 26, 2019

(65) Prior Publication Data
US 2020/0405177 A1    Dec. 31, 2020

(51) Int. Cl.
*A61B 5/055* (2006.01)
*A61B 6/04* (2006.01)
*A61G 13/12* (2006.01)
*A61N 7/00* (2006.01)

(52) U.S. Cl.
CPC ............ *A61B 5/055* (2013.01); *A61B 6/0407* (2013.01); *A61G 13/1245* (2013.01); *A61G 13/125* (2013.01); *A61N 7/00* (2013.01); *A61N 2007/0078* (2013.01)

(58) Field of Classification Search
CPC .. A61B 5/055; A61B 6/0407; A61G 13/1245; A61G 13/125; A61N 7/00; A61N 2007/0078
See application file for complete search history.

(56) References Cited

U.S. PATENT DOCUMENTS

| | | | | |
|---|---|---|---|---|
| 5,178,148 A | * | 1/1993 | Lacoste | A61B 5/1073 600/439 |
| 5,474,071 A | * | 12/1995 | Chapelon | A61B 17/22004 600/439 |
| 6,210,314 B1 | * | 4/2001 | Ein-Gal | A61N 1/403 600/3 |

(Continued)

FOREIGN PATENT DOCUMENTS

CA         2881665 A1 *  2/2014   ......... A61G 13/0063

OTHER PUBLICATIONS

ISA, "International Search Report", PCT/CA2020/050881, dated Aug. 31, 2020.

*Primary Examiner* — David R Hare
*Assistant Examiner* — Alexis Felix Lopez
(74) *Attorney, Agent, or Firm* — Intrinsic Law Corp.

(57) ABSTRACT

An MRI-compatible system for supporting a patient during a medical procedure includes a frame, first and second platforms, a cooling device support, a therapeutic-applicator-positioning-system support, and a pair of leg rests. The first platform is configured to support the patient. The second platform is disposed between the foot end of the frame and the first platform. The cooling device support and the therapeutic-applicator-positioning-system support are mounted on the second platform. The cooling device support positions and releasably secures a cooling device. The therapeutic-applicator-positioning-system support releasably secures a therapeutic applicator positioning system. Each leg rest includes a leg support and a foot support. The leg rests are disposed on the frame and are configured to be slidably positioned towards the head end or towards the foot end of the frame.

21 Claims, 8 Drawing Sheets

(56) References Cited

U.S. PATENT DOCUMENTS

| | | | | |
|---|---|---|---|---|
| 6,684,095 | B1* | 1/2004 | Bonutti | A61B 6/0485 600/415 |
| 7,452,357 | B2* | 11/2008 | Vlegele | A61B 90/10 600/439 |
| 7,600,281 | B2* | 10/2009 | Skripps | A61G 13/0054 5/600 |
| 7,676,255 | B2* | 3/2010 | Wang | A61B 6/0478 600/415 |
| 7,711,407 | B2* | 5/2010 | Hughes | A61B 5/055 600/417 |
| 9,056,042 | B2* | 6/2015 | Russell | A61G 13/1245 |
| 10,682,156 | B2* | 6/2020 | Rahman | A61B 6/547 |
| 2005/0080333 | A1 | 4/2005 | Piron et al. | |
| 2007/0039101 | A1* | 2/2007 | Luginbuhl | A61B 6/4417 5/600 |
| 2011/0301508 | A1 | 12/2011 | Sethuraman et al. | |
| 2015/0080705 | A1* | 3/2015 | Partanen | A61B 5/015 600/411 |
| 2015/0265216 | A1* | 9/2015 | Andrews | A61B 18/04 128/845 |
| 2017/0120072 | A1* | 5/2017 | Van De Wardt | A61B 34/20 |
| 2018/0289575 | A1* | 10/2018 | Hiratsuka | A61B 6/547 |
| 2019/0231306 | A1* | 8/2019 | Marcil | A61B 8/085 |

* cited by examiner

MRI-COMPATIBLE PATIENT SUPPORT SYSTEM

TECHNICAL FIELD

This application relates generally to patient support systems for MRI-guided therapy treatment.

BACKGROUND

Ultrasonic transducers have been employed in ultrasound therapy systems to achieve therapeutic heating of diseased and other tissues. Arrays of ultrasound transducers operating to form a beam of ultrasonic energy cause a conversion of sound to thermal energy in the affected tissue areas or treatment volumes, and a subsequent beneficial rise in the temperature in the treatment volumes.

In image-guided ultrasound therapy systems, a patient and the ultrasound therapy apparatus, including an ultrasound positioning apparatus, are generally disposed in an imaging volume such as a magnetic resonance imaging (MRI) apparatus, which allows guidance of the applicator placement, and in addition allows monitoring of the treatment effect on the tissue by providing real-time data from which temperature maps can be calculated. A clinical operator can then monitor the progress of the therapy within the treatment volume or diseased tissue and manual or automated changes can be made to the ultrasound power signals based on input from the results and progress of the treatment. With proper monitoring of the heating effect, ultrasound therapy systems can be used to treat harmful cells and to controllably destroy tumors while minimizing damage to healthy tissue.

Present systems are not optimized or even sometimes compatible for use with MRI-guided ultrasonic thermal therapy processes. Patient comfort, system performance, cost and logistic considerations are some of the considerations addressed below.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a system for supporting a patient, comprising: a frame having a head end and a foot end; a first platform mounted on the frame, the first platform configured to support the patient; a second platform mounted on the frame, the second platform disposed between the foot end of the frame and the first platform; a cooling device support that positions and releasably secures a cooling device, the cooling device support mounted on the second platform at a first attachment point; a therapeutic-applicator-positioning-system support configured and arranged to support and releasably secure a therapeutic applicator positioning system, the therapeutic-applicator-positioning-system support mounted on the second platform at a second attachment point, the second platform being lockable with respect to the frame to secure the therapeutic applicator positioning system at a desired position between the head end and the foot end of the frame; and a pair of leg rests, each leg rest comprising a leg support and a foot support, each leg rest being disposed on the frame and configured to be slidably positioned towards the head end or towards the foot end of the frame, wherein the system is constructed of a magnetic resonance imaging (MRI) compatible material suitable for use in an MRI environment during a medical procedure.

In one or more embodiments, the first attachment point is disposed laterally from the second attachment point. In one or more embodiments, the cooling device support comprises part of a ball-and-socket assembly for mechanically coupling and providing support to the cooling device. In one or more embodiments, the cooling device comprises an endorectal cooling device.

In one or more embodiments, the cooling device support is attached to an articulated stand that is repositionable in three dimensions. In one or more embodiments, the cooling device support is pivotably attached to the articulated stand. In one or more embodiments, the cooling device support can be slidably positioned within a slot in the second platform, the slot extending parallel to a frame axis that extends from the head end to the foot end of the frame. In one or more embodiments, a position of the cooling device support is lockable within the slot.

In one or more embodiments, the therapeutic applicator positioning system comprises an ultrasound therapy applicator positioning system configured and arranged to support an ultrasound therapy applicator and to position the ultrasound therapy applicator in more than one degree of freedom. In one or more embodiments, the therapeutic-applicator-positioning-system support includes anchors that releasably secure the therapeutic applicator positioning system to the therapeutic-applicator-positioning-system support. In one or more embodiments, one of the anchors comprises a spring-loaded latch.

In one or more embodiments, the second platform is configured to be slidably positioned towards the head end or towards the foot end of the frame. In one or more embodiments, the second platform includes a slot to slidably position the second platform with respect to the frame. In one or more embodiments, a position of the second platform is lockable within the slot. In one or more embodiments, the second platform is moveable along a rail on the frame, the rail parallel to a frame axis that extends from the head end to the foot end of the frame.

In one or more embodiments, the leg support and the foot support of each leg rest is disposed on a leg rest support stand. In one or more embodiments, each leg rest support stand includes a knee support arm mechanically coupled to the knee support and a foot support arm mechanically coupled to the foot support. In one or more embodiments, each leg rest support stand is slidably positionable along a leg rest positioning slot defined in a leg rest platform, the leg rest platform mounted on the frame. In one or more embodiments, each leg rest includes a leg support pad and a foot support pad disposed on the leg support and the foot support, respectively.

Yet other embodiments are directed to a patient support system for supporting a patient during a thermal therapy procedure, the system comprising a patient support platform, having a first end proximal to a patient's head and a second end proximal to a patient's feet, the support platform further configured and arranged to support at least a portion of a patient's upper body in a horizontal supine position; a pair of leg supports configured and arranged to support at least a portion of a patient's lower body or legs; a thermal therapy positioning rail including an elongated guide for slidably positioning an articulated thermal therapy applicator along an axis directed between said first end and said second end, and further configured and arranged to lockably secure said thermal therapy applicator in a determined position along said axis; and a cooling apparatus anchor point, mechanically fixing an articulated member at said anchor point on one end of the articulated member.

BRIEF DESCRIPTION OF THE DRAWINGS

For a fuller understanding of the nature and advantages of the present concepts, reference is made to the following detailed description of preferred embodiments and in connection with the accompanying drawings.

DETAILED DESCRIPTION

Figure 1:
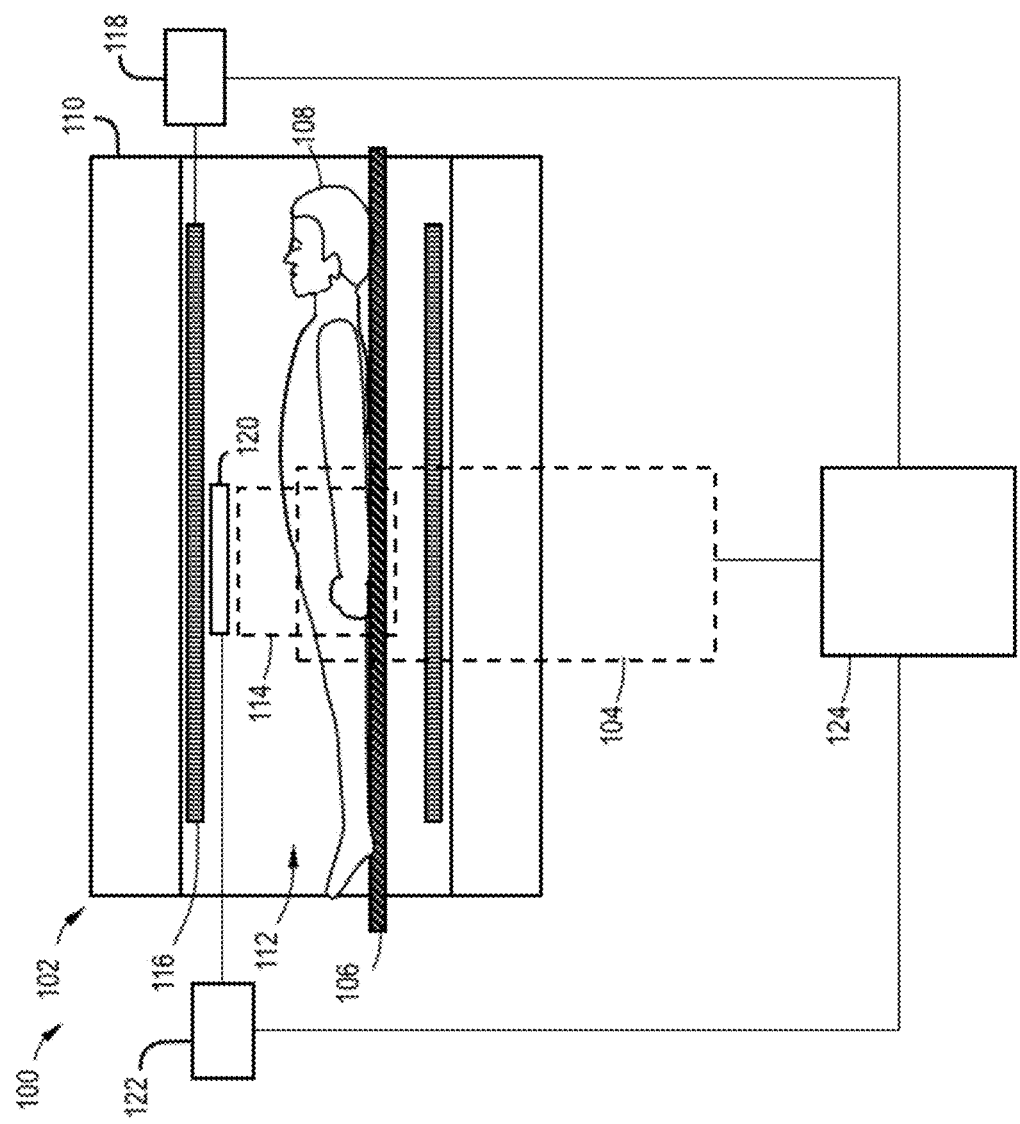
FIG. 1 is a diagram of one type of system in which at least some of the apparatus and/or methods disclosed herein are employed, in accordance with at least some embodiments.

FIG. 1 is a diagram of one type of medical system 100 in which at least some of the apparatus, systems, and/or methods disclosed herein are employed, in accordance with at least some embodiments. The system 100 includes a patient support system 106 (on which a patient 108 is shown), a magnetic resonance system 102 and an image guided energy delivery system 104.

The magnetic resonance system 102 includes a magnet 110 disposed about an opening 112, an imaging zone 114 in which the magnetic field is strong and uniform enough to perform magnetic resonance imaging, a set of magnetic field gradient coils 116 to change the magnetic field rapidly to enable the spatial coding of MRI signals, a magnetic field gradient coil power supply 118 that supplies current to the magnetic field gradient coils 116 and is controlled as a function of time, a transmit/receive coil 120 (also known as a "body" coil) to manipulate the orientations of magnetic spins within the imaging zone 114, a radio frequency transceiver 122 connected to the transmit/receive coil 120, and a computer 124, which performs tasks (by executing instructions and/or otherwise) to facilitate operation of the MRI system 102 and is coupled to the radio frequency transceiver 122, the magnetic field gradient coil power supply 118, and the image guided energy delivery system 104.

Figure 2:
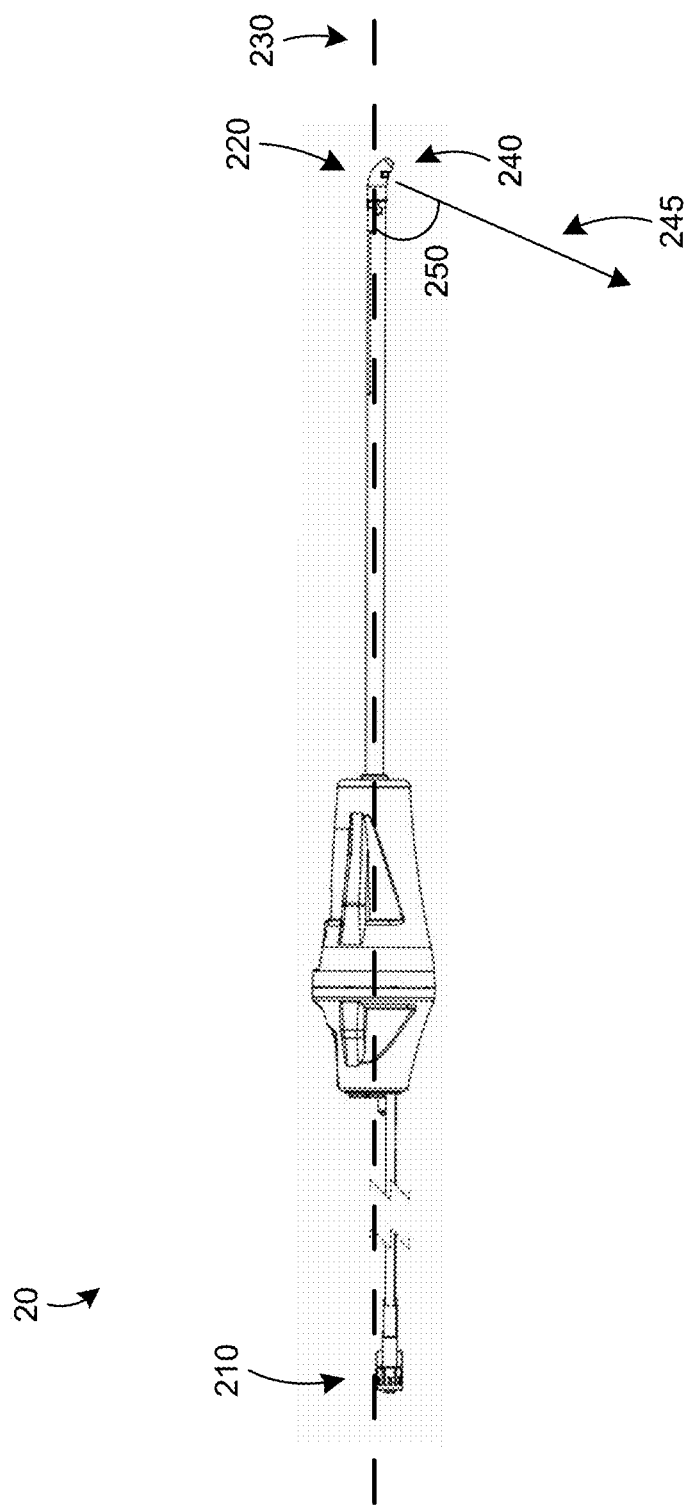
FIG. 2 illustrates an example of an ultrasound applicator that can be used in the system illustrated in FIG. 1.

The image guided energy delivery system 104 includes a therapeutic applicator, such as an ultrasound applicator, to perform image guided therapy (e.g., thermal therapy) in multiple angular directions to treat a treatment region. An example of a therapeutic applicator that can be used in system 100 is ultrasound applicator 20 illustrated in FIG. 2. The ultrasound applicator 20 can be mounted on a positioning apparatus, embodiments of which are described herein.

The applicator 20 has a proximal end 210 and a distal end 220. The proximal and distal ends 210, 220 define an axis 230 along which the applicator 20 is elongated. One or more ultrasound source elements 240 (e.g., transducers) are disposed near, towards, and/or at the distal end 220 of the applicator. The ultrasound source element(s) 240 are oriented to face outwardly such that the ultrasound source element(s) 240 radiate ultrasonic energy 245 outwardly, from the applicator 20 and axis 230, along an azimuthal direction about the axis 230. The azimuthal direction can be defined by the angle 250 formed between the radiation/propagation direction of ultrasonic energy 245 from one of the ultrasound source element(s) 240 and the axis 230.

Returning to FIG. 1, the MRI computer 124 can include more than one computer in some embodiments, which can be dedicated for the MRI system 102. In at least some embodiments, the MRI computer 124 and/or one or more other computing devices (not shown) in and/or coupled to the system 100 may also perform one or more tasks (by executing instructions and/or otherwise) to implement one or more aspects and/or embodiments disclosed herein (or portion(s) thereof) to control the rotational position and insertion-retraction position of the therapeutic applicator, for example with respect to a target volume.

One or more of the computers, including computer 124, can include a treatment plan for the patient 108 that includes the target treatment region and the desired or minimal energy (e.g., thermal) dose for the target treatment region. The computer(s) can use images from the magnetic resonance system 102 to image guide the rotational position and insertion-retraction position of the therapeutic applicator. In some embodiments, one or more dedicated computers control the image guided energy delivery system 104. Some or all of the foregoing computers can be in communication with one another (e.g., over a local area network, a wide area network, a cellular network, a WiFi network, or other network), for example through a software-controlled link to a communication network.

Figure 3:
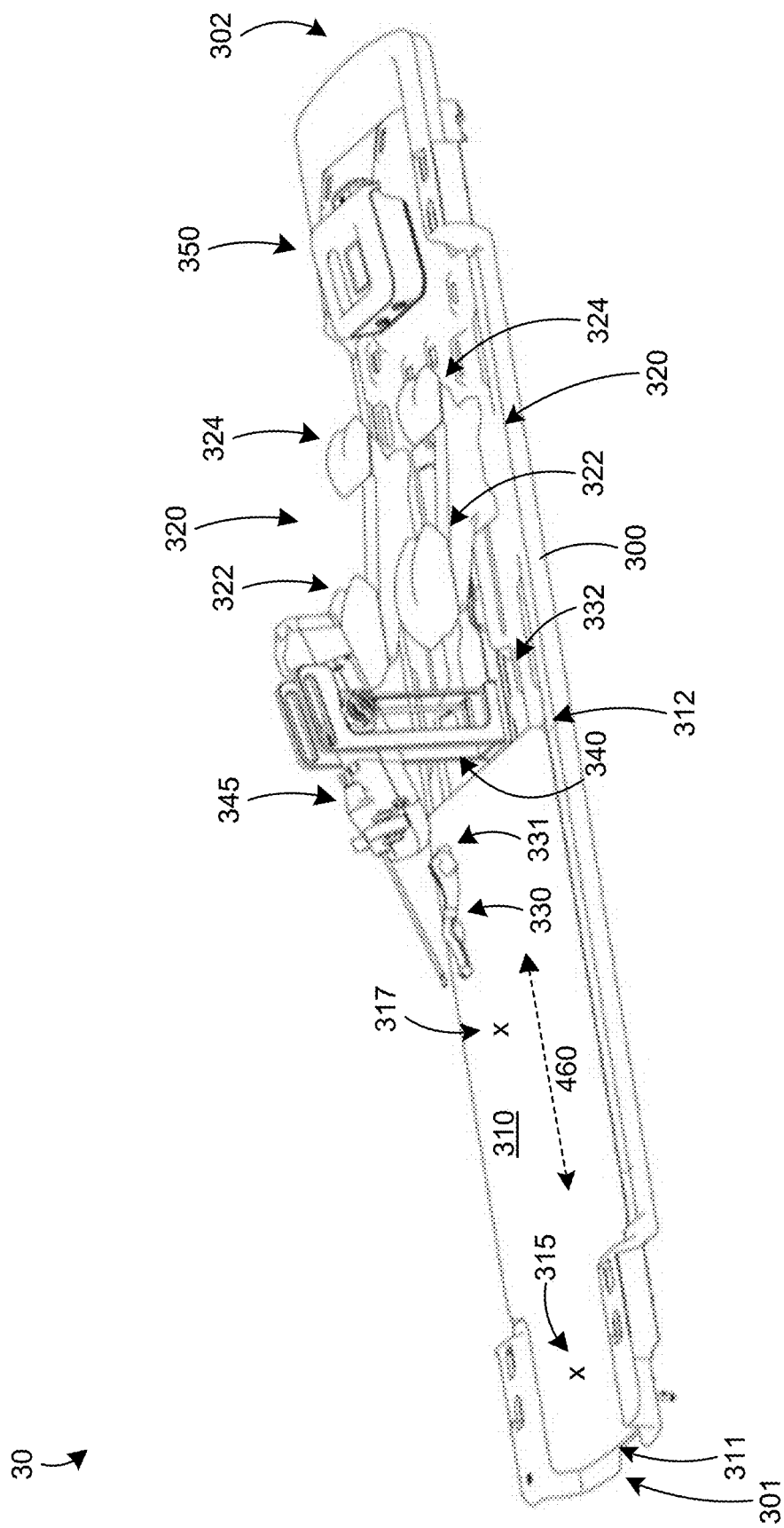
FIG. 3 is a perspective view of a patient support system according to one or more embodiments.

FIG. 3 is a perspective view of a patient support system 30 according to one or more embodiments. The patient support system 30 can be the same as and/or an embodiment of the patient support system 106, discussed above.

The patient support system 30 extends between a head end 301 and a foot end 302 generally being nearer to a patient's head and feet, respectively, when said patient is lying on the patient support system. A frame or platform 300 may be available as a separate bed such as a MRI patient support bed or similar structural support and may be used to support, carry or secure one or more components of the patient support system 30. A patient support platform 310 is attached to the frame 300. In optional embodiments, the patient support platform 310 may be constructed integrally with a frame 300, or mounted to support platform 450, but this is not limiting, and in other embodiments the support platform 310 is independent of the underlying frame 300 which can be provided by other vendors separately. The patient support platform 310 can have a planar or a substantially planar surface (e.g., within 5-10° of a plane) that supports the patient's torso and head while the patient lies on the patient support system 30 (e.g., in a supine position on the patient support platform 310) during therapeutic treatment, such as MRI-guided therapeutic ultrasound treatment. The patient's head can be disposed in an optional head recess 311 defined in a head end 301 of the patient support platform 310. In addition, an optional head indicator 315 can be disposed at the head end 301 of the patient support platform 310 to indicate an optimal location for the patient's head. The head indicator 315 can include a marking (e.g., an "X," a cross, a line, etc.), raised or lowered features, one or more colors, and/or other indicators.

Figure 6:
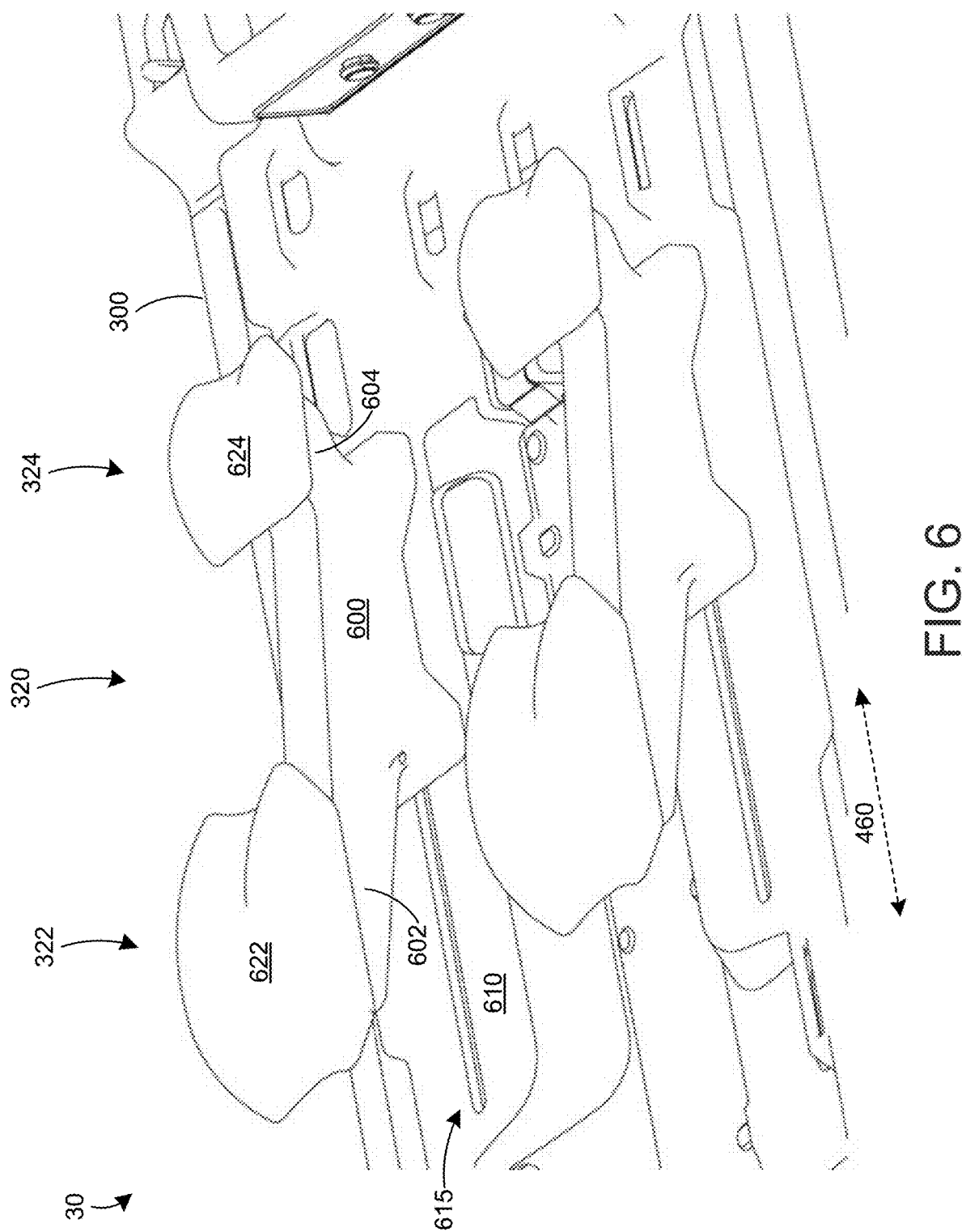
FIG. 6 is a detailed perspective view of the leg rests on the patient support system illustrated in FIG. 1, according to one or more embodiments.

The patient's legs can be supported by a pair of leg rests 320. Each leg rest 320 includes a knee support 322 and a foot support 324. The knee support 322 and/or the foot support 324 can include pads, cushions, pillows, and/or another object to improve patient comfort (e.g., optional under-leg support pad 622 and optional under-foot support pad 624, respectively, as illustrated in FIG. 6). The pads, cushions, pillows, etc. can include foam, gel, and/or another soft and/or supportive material. In one aspect, the leg or knee rests may be elevated higher than an elevation of the patient support platform 310 so as to cause a desired lift or bend in the patient's leg position during a therapeutic procedure.

The patient support system 30 includes attachment points to removably secure one or more therapeutic devices for treating the patient such as during a medical procedure. For example, a first attachment point 331 is disposed on the patient support platform 310 to removably secure and position a cooling device 330. The first attachment point 331 may be secured to a support platform at 450. But those skilled in the art will appreciate that a variety of options for configuring and supporting these components are also possible. The cooling device 330 can include (or can be) an endorectal cooling device that cools the rectum and surrounding tissue while a heat-inducing therapy is applied to nearby tissue or organ (e.g., to the prostate).

The first attachment point 331 can be located at or proximal to a torso end 312 of the patient support platform 310 or to the platform at 450 as illustrated such that the cooling device 330 can be inserted into the patient's rectum while the patient lies (e.g., in a supine position) on the patient support platform 310.

In some embodiments, the first attachment point 331 is moveable with respect to the frame 300 if used. For example, the first attachment point 331 can slide towards or away from the head end 301 of the patient support platform 310 to align the cooling device 330 with the patient's rectum (e.g., based on the patient's height). In addition, the first attachment point 331 can be secured to an articulated member (not shown but illustrated further below) to allow the cooling device 330 to pivot with respect to the patient support platform 310 to adjust the insertion/removal angle of the cooling device 330 into/out of the patient's rectum. In some embodiments, a prostate indicator 317 can be disposed on the patient support platform 310 to indicate an optimal or desired position for the patient's prostate or buttocks. For example, the first and second attachment points 331, 332 and/or the cooling device 330 and the therapeutic applicator positioning system 340 (described below), respectively, can be adjustably positioned relative to the prostate indicator 317. The prostate indicator 317 can include a marking (e.g., an "X," a line, a cross, etc.), raised or lowered features, one or more colors, and/or other indicators.

A second attachment point 332 may be mechanically coupled to any suitable location on support platform 310, 450 or supporting frame 300 to removably secure and position a therapeutic applicator positioning system 340 which can position a therapeutic applicator 345 in multiple degrees of freedom. An example of the therapeutic applicator positioning system 340 is described in U.S. patent application Ser. No. 16/248,246, titled "Therapeutic Applicator Positioning System With Passive and Active Positioning," filed on Jan. 15, 2019, which is hereby incorporated by reference. For example, the therapeutic applicator positioning system 340 can adjust the elevational position of the therapeutic applicator 345 with respect to the frame 300, the axial position of the therapeutic applicator 345 with respect to a frame axis 460 that extends from the head end 301 to the foot end 302 of the frame 300, and/or the angular position (e.g., azimuthal position) of the therapeutic applicator 345 (e.g., with respect to the plane of the patient support platform 310).

The therapeutic applicator 345 can deposit energy (e.g., ultrasound, infrared, electromagnetic, etc.) onto or into the patient, such as into the patient's prostate to treat a tumor. For example, the therapeutic applicator 345 can be inserted transurethrally so that ultrasound elements disposed on the tip of the therapeutic applicator 345 are disposed near the prostate.

In some embodiments, the second attachment point 332 is moveable with respect to the frame 300. For example, the second attachment point 332 can slide towards or away from the head end 301 of the frame 300 to position the therapeutic applicator positioning system 340 proximal at a desired location proximal to the patient's groin (e.g., so a portion of the therapeutic applicator 345 can be inserted into the patient's urethra). The second attachment point 332 can be slide in a slot or on a rail to position (e.g., lockably position) the second attachment point 332 with respect to the frame 300. It should be understood that in other embodiments the positional adjustments mentioned, e.g., by sliding the present components along a head-to-foot axial position can occur using sliding members within the positioning system and its main platform structure.

A positioning system controller 350 is optionally disposed on the frame 300 or platform 450. The positioning system controller 350 includes one or more processors that generate control signals to adjust the position and/or orientation of the therapeutic applicator 345 using the therapeutic applicator positioning system 340, and to rotate the therapeutic applicator 345 (e.g., using therapeutic applicator positioning system 340) while therapeutic energy is emitted from the therapeutic applicator 345. The positioning system controller 350 can also generate the energy (e.g., ultrasound) that is emitted from the therapeutic applicator 345. Thus, the positioning system controller 350 is in electrical communication (e.g., via one or more wires disposed on or in the support body 300) with the therapeutic applicator positioning system 340 and/or with the therapeutic applicator 345.

Figure 4:
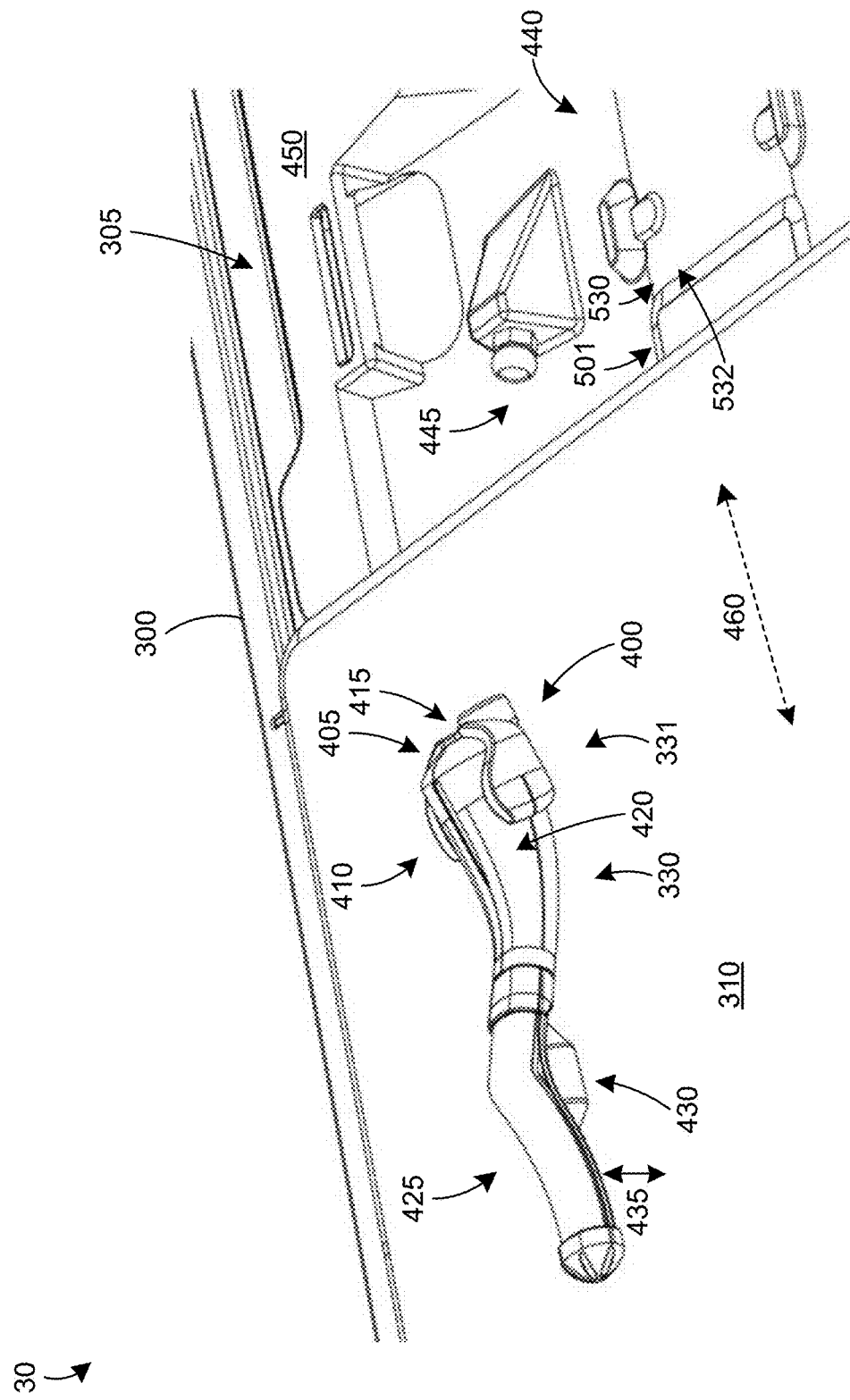
FIG. 4 is a detailed perspective view of the first and second attachment points on the patient support system illustrated in FIG. 1, according to one or more embodiments.

FIG. 4 is a detailed perspective view of the first and second attachment points 331, 332 shown above on the patient support system 30 according to one or more embodiments. The first attachment point 331 includes a cooling device support 400 that forms a portion of a mechanical coupling, such as a ball-and-socket assembly, a helm joint, a rod end bearing, or other mechanical coupling, with the cooling device 330. For example, in FIG. 4 the cooling device support 400 defines a cavity 405 that forms the female portion of a ball-and-socket assembly 410. The male portion of the ball-and-socket assembly 410 is formed by the handle 420 of the cooling device 330. In other embodiments, the handle 420 can be configured to form the female portion of the ball-and-socket assembly 410 (or other mechanical coupling) and the cooling device support 400 can be configured to form the male portion of the ball-and-socket assembly 410 (or other mechanical coupling). The handle 420 is removably secured in the cooling device support 400 so that the cooling device 330 can be removed as needed for maintenance or cleaning, or for installing a new or disinfected cooling device prior to the next therapeutic procedure. An optional opening 415 is formed in the cooling device support 400 in alignment with the proximal end of the handle 420 to allow electrical and/or fluid connections to pass into the cooling device 330. The cooling device 330 may include an end 425 (insertion end) that is inserted into a patient's cavity to cool tissue proximal thereto. The cooling device 330 may be elevated above the patient support platform by some distance 435. Other components 430 of the cooling device 330 may be disposed along the device to include optional sensors, operator controls or such members.

The cooling device support 400 can be pivotably attached to the patient support platform 310 or to any other supporting structure or frame, which can allow the cooling device support 400—and hence the cooling device 330 in the ball-and-socket assembly 410—to pivot towards or away from the patient support platform 310. This pivoting feature can allow the clinical operator to angularly align the cooling device 330 with the patient's rectum (or other target) for insertion therein. While the cooling device 330 is inserted into the patient's rectum, the cooling device 330 can pivot in response to patient movement which can improve patient comfort. Alternatively, the pivot angle of the cooling device support 400 can be locked or secured, such as after the cooling device 330 is inserted into the patient's rectum.

In some embodiments, the cooling device 330 is coupled with a flexible mechanical coupling, a lockable mechanical coupling, or directly to the patient support platform 310. In one non-limiting example, the cooling device support 400 can be disposed on a groove, rail, or track on the patient support platform 310 or frame 300 to allow the cooling device support 400 to move (e.g., translate) towards or away from the head end 301 of the support platform 310 parallel to the frame axis 460. This can allow the clinical operator to further position and customize the position and orientation/angle of the cooling device 330 with respect to a first target location (e.g., rectum) on or in the patient. The cooling device support 400 can be lockably positioned within the optional groove, rail, or track to secure the cooling device 330 at a desired position (e.g., with respect to the first target location).

Figure 7:
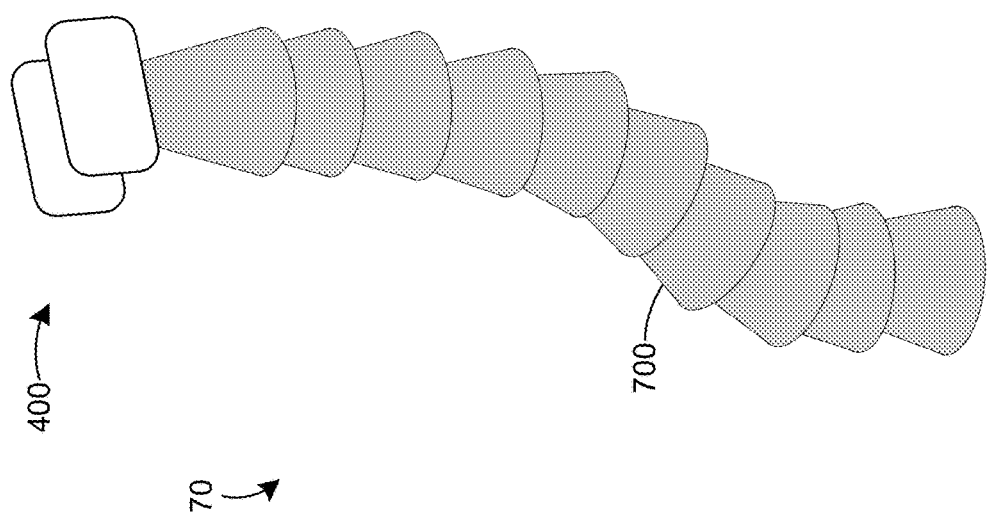
FIG. 7 is a side view of an articulated stand according to one or more embodiments.

In some embodiments, the cooling device support 400 can be disposed on an articulated stand 70 that includes a plurality of interlinking ball-and-socket joints 700, as illustrated in FIG. 7. The connection between adjacent ball-and-socket joints 700 is adjustable, which allows the stand 70 to bend in up to 3 dimensions (e.g., horizontally in the x- and/or y-directions, and/or vertically in the z-direction) to position the cooling device support 400 at a desired position with respect to the patient, such as proximal to the patient's rectum. In addition, the bending of the stand 70 can adjust the pivot angle of the cooling device support 400 and the corresponding insertion angle of the attached cooling device 330 (e.g., to angularly align with the patient's rectum). The ball-and-socket joints 700 are friction-fitted such that they maintain their position once adjusted. Connections members as shown in FIG. 7 can be used to couple between points 415 and 445 of FIG. 4 in some embodiments.

The stand 70 can be directly attached to a male connector 445 on the therapeutic-applicator-positioning-system platform 450, which can function as the first attachment point 331. When the male connector 445 functions as the first attachment point 331, the first attachment point 331 is disposed laterally from the second attachment point 332 (e.g., perpendicular to frame axis 460). The male connector 445 can mechanically engage a female connector on the bottom of the stand 70. In other embodiments, the male connector 445 can be replaced with a female connector that can mechanically engage a male connector on the bottom of the stand 70. In some embodiments, the stand 70 can be attached to a platform or other surface (e.g., via male connector 445) that can be adjustably attached to the patient support platform 310 (e.g., along a rail, groove, etc.). In some embodiments, the male connector 445 can include a snap lock, a quick-release lock, a quick-disconnect lock, or other releasable mechanical coupling. The male connector 445 can be fixedly or adjustably (e.g., slidably) attached to the therapeutic-applicator-positioning-system platform 450. For example, the male connector 445 can be slidably adjusted within a slot in the therapeutic-applicator-positioning-system platform 450 that is parallel to the frame axis 460. The male connector 445 can be lockably positioned at a desired position in the slot.

Figure 5:
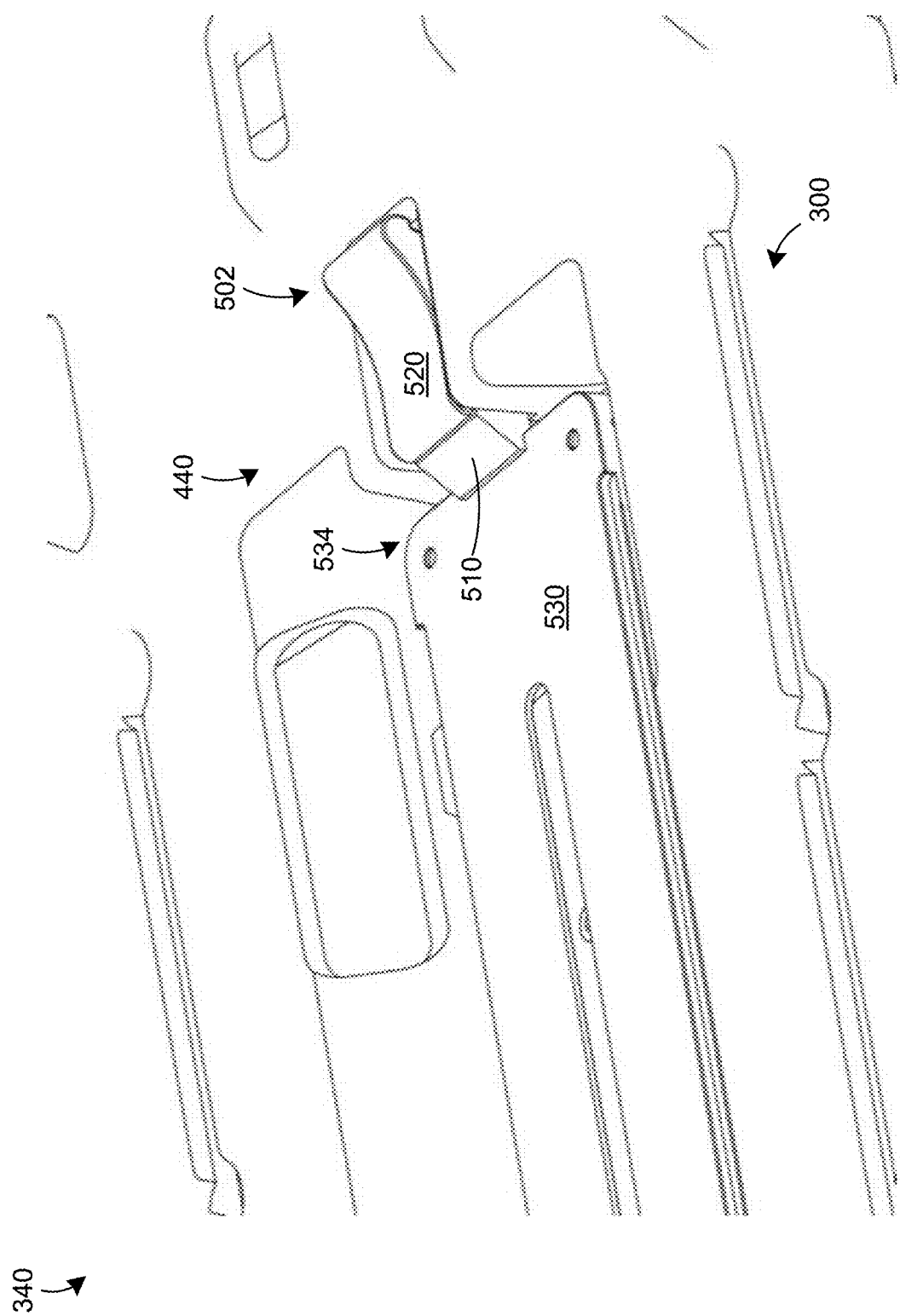
FIG. 5 is a detailed perspective view of a therapeutic applicator positioning system that can be releasably secured to the patient support system illustrated in FIG. 1, according to one or more embodiments.

The second attachment point 332 includes a therapeutic-applicator-positioning-system support 440 that forms a portion of a mechanical coupling with the therapeutic applicator positioning system 340. For example, in FIGS. 4 and 5 the therapeutic-applicator-positioning-system support 440 includes first and second anchors 501, 502 that releasably mechanically couple the therapeutic applicator positioning system 340 to the frame 300 or support platform at 450 of the patient support system 30. The second anchor 502 includes a spring-loaded latch 510 that can be mechanically released by depressing an actuator 520.

In operation, a head end 532 of a base 530 of the therapeutic applicator positioning system 340 is inserted into the first anchor 501 of the therapeutic-applicator-positioning-system support 440 to pivotably attach the base 530 to the therapeutic-applicator-positioning-system support 440. The first anchor 501 can include a female anchor portion (e.g., a pocket, recess, etc.) that can releasably mechanically engage a corresponding male anchor portion (e.g., a hook or other male projection) disposed on the head end 532 of the base 530. In other embodiments, the first anchor 501 can be configured to include a male anchor portion and the head end 532 can be configured to include a female portion of the releasable mechanical coupling.

After the head end 532 of the base 530 is pivotably attached to the first anchor 501, the foot end 534 of the base 530 is lowered to mechanically engage the spring-loaded latch 510. The spring-loaded latch 510 is angled to cause it to depress towards the actuator 520 when the foot end 534 of the base 530 is lowered, allowing the foot end 534 of the base 530 to pivot against the frame 300. When the foot end 534 of the base 530 is pivoted against the frame, the spring-loaded latch 510 is pushed back towards the head end 532 of the base 530 to releasably mechanically secure the foot end 534 in the second anchor 502. In this embodiment, the spring-loaded latch 510 can function as the female portion of a mechanical coupling and the foot end 534 can function as the male portion. In other embodiments, the spring-loaded latch 510 can be configured to function as the male portion and the foot end 534 can be configured to function as the female portion of the releasable mechanical coupling.

To release the base 530 from the first and second anchors 501, 502, the actuator 520 can be mechanically depressed (e.g., manually) to retract the spring-loaded latch 510, allowing the foot end 534 of the base 530 to be lifted out of the second anchor 502. The head end 532 of the base 530 can then be lifted upwards to release the base 530 from the first anchor 501.

In other embodiments, the base 530 of the therapeutic applicator positioning system 340 can be configured to form the male portion of the mechanical coupling and the therapeutic-applicator-positioning-system support 440 can be configured to form the female portion of the mechanical coupling. The mechanical coupling can include a snap lock, a quick-release lock, a quick-disconnect lock, or other releasable mechanical coupling.

Figure 8:
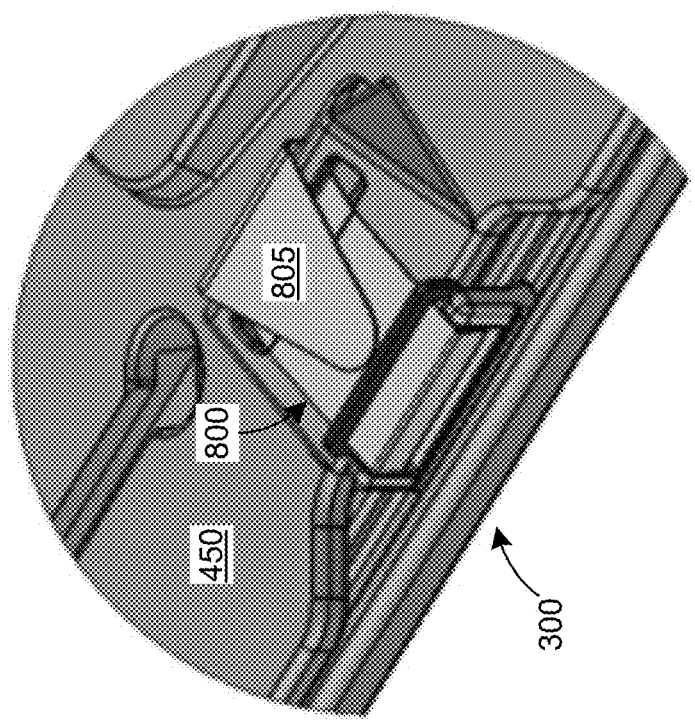
FIG. 8 is a perspective view of a strap that releasably attaches the therapeutic-applicator-positioning-system platform and/or the patient support platform to the frame, according to one or more embodiments.

The therapeutic-applicator-positioning-system support 440 and the male connector 445 of the first attachment point 331 can be disposed on a therapeutic-applicator-positioning-system platform 450 that is mechanically coupled to the frame 300. In some embodiments, the therapeutic-applicator-positioning-system platform 450 can slidably engage the frame 300. For example, the therapeutic-applicator-positioning-system platform 450 can engage grooves or rails 305 on the frame 300 to slidably position the therapeutic-applicator-positioning-system platform 450 with respect to the frame axis 460. By slidably positioning the therapeutic-applicator-positioning-system platform 450 along the frame axis 460, the clinical operator can position the therapeutic-applicator-positioning-system support 440, and hence the therapeutic applicator positioning system 340, at a desired position between the head end 301 to the foot end 302 of the frame 300. Thus, the clinical operator can customize the position of the therapeutic applicator positioning system 340 and the therapeutic applicator 345 at a desired initial position with respect to a second target location on or in the patient, such as the patient's groin or urethra. When the therapeutic applicator positioning system 340 and the therapeutic applicator 345 are located at the desired initial position, the position of the therapeutic-applicator-positioning-system platform 450 on the frame 300 can be locked or secured. In some embodiments, the therapeutic-applicator-positioning-system platform 450 and/or the patient support platform 310 is/are releasably attached to the frame 300 by one or more straps 800 as illustrated in FIG. 8. Each strap 800 can include a hook-and-loop fastener to attach an end 805 of the strap 800 to the rest of the strap 800. In addition or in the alternative, the frame 300 can be releasably attached to an MRI-compatible bed by one or more straps, such as straps 800 (e.g., in the same manner as illustrated in FIG. 8).

FIG. 6 is a detailed perspective view of the leg rests 320 on the patient support system 30, according to one or more embodiments. The knee support 322 and foot support 324 of each leg rest 320 are disposed on a leg rest support stand 600 which includes a knee support arm 602 that is mechanically coupled to the knee support 322 and a foot support arm 604 that is mechanically coupled to the foot support 324. The knee support 322 and foot support 324 include an optional under-leg support pad 622 and an optional under-foot support pad 624, respectively. The under-leg support pad 622 and under-foot support pad 624 can be removably attached to the knee support 322 and foot support 324, respectively, such as by snaps, hook-and-loop fasteners, an adhesive, or other attachment mechanism.

The leg rest support stand 600 can be slidably positioned along a leg rest positioning slot 615 defined in a leg rest platform 610, which is mounted on the frame 300. The slot 615 extends parallel to the frame axis 460. A complementary leg rest positioning projection is disposed on the bottom of the leg rest support stand 600 to slidably engage the slot 615. The leg rest positioning projection can include a rod, a pin, a rail, or other projection. The leg rest support stand 600 can be locked or secured at a desired position along the slot 615 (e.g., towards the head end 301 or the foot end 302 of the frame 300), for example to align the knee supports 322 and foot supports 324 with the patient's knees and feet, respectively. The bottom of the leg rest support stand 600 and/or the top of the leg rest platform 610 can include grooves, detents, or other features that prevent relative movement therebetween. In addition or in the alternative, the weight of the patient's legs on the leg rest support stand 600 can prevent the leg rest support stand 600 from moving with respect to the leg rest support platform 610. In some embodiments, the knee support 322 and/or foot support 324 can be positionally adjusted independently (e.g., vertically and/or horizontally) to customize its/their position(s) for the patient.

The patient support system 30 can be formed, molded, casted, or machined out of one or more MRI-compatible materials. Examples of such MRI-compatible materials include non-ferrous metals (e.g., aluminum, titanium, brass, copper) and non-metals such as polymers including plastics, composites, and/or reinforced engineering plastics.

It can be seen therefore that the present disclosure provides for a useful patient support system for supporting a patient during a thermal therapy procedure, for example supporting a supine lying patient on the platform during an ultrasound, RF, laser or other thermal therapy treatment procedure. In an aspect, the system comprises a patient support platform or substantially flat and horizontal panel 310, having a first end proximal to a patient's head and a second end proximal to a patient's feet on which the patient may be laid. The support platform is further configured and arranged to support at least a portion of a patient's upper body in a horizontal supine position on the platform's upper surface. In addition, some aspects provide for an adjustable (moveable) pair of leg supports configured and arranged to support at least a portion of a patient's lower body or legs, for example at or near the patient's knees. In one embodiment, the leg supports are elevated above the horizontal surface of the support platform so that the patient's legs or knees are somewhat raised with respect to a height of the platform 310. In addition, in some aspects a thermal therapy positioning rail is coupled to the system and includes an elongated guide for slidably positioning an articulated thermal therapy applicator along an axis directed between said first end and said second end, and further configured and arranged to lockably secure said thermal therapy applicator in a determined position along said axis. In an optional aspect, a cooling apparatus anchor point, mechanically fixing an articulated member at said anchor point on one end of the articulated member is also provided. The system therefore allows for resting and supporting and positioning a patient optimally for receiving a thermal therapy applicator or cooling device, such as an ultrasound applicator or a rectal cooling device, into a cavity of the patient. The device(s) can then be delicately positioned and/or secured during a procedure.

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

What is claimed is:

1. A system for supporting a patient, comprising:
   a frame having a head end and a foot end;
   a first platform mounted on the frame, the first platform configured to support the patient;
   a second platform mounted on the frame, the second platform disposed between the foot end of the frame and the first platform;
   a cooling device support that positions and releasably secures a cooling device, the cooling device support mounted on the second platform at a first attachment point;
   a therapeutic-applicator-positioning-system support configured and arranged to support and releasably secure a therapeutic applicator positioning system, the therapeutic-applicator-positioning-system support mounted on the second platform at a second attachment point, the second platform being lockable with respect to the frame to secure the therapeutic applicator positioning system at a desired position between the head end and the foot end of the frame; and
   a pair of leg rests, each leg rest comprising a leg support and a foot support, each leg rest being disposed on the frame and configured to be slidably positioned towards the head end or towards the foot end of the frame,
   wherein the system is constructed of a magnetic resonance imaging (MRI) compatible material suitable for use in an MRI environment during a medical procedure; and
   wherein the therapeutic-applicator-positioning-system support includes anchors that releasably secure the therapeutic applicator positioning system to the therapeutic-applicator-positioning-system support.

2. The system of claim 1, wherein the first attachment point is disposed laterally from the second attachment point.

3. The system of claim 1, wherein the cooling device support comprises part of a ball-and-socket assembly for mechanically coupling and providing support to the cooling device.

4. The system of claim 3, wherein the cooling device comprises an endorectal cooling device.

5. The system of claim 1, wherein the cooling device support is attached to an articulated stand that is repositionable in three dimensions.

6. The system of claim 5, wherein the cooling device support is pivotably attached to the articulated stand.

7. The system of claim 1, wherein the cooling device support is slidably positionable within a slot in the second platform, the slot extending parallel to a frame axis that extends from the head end to the foot end of the frame.

8. The system of claim 7, wherein a position of the cooling device support is lockable within the slot.

9. The system of claim 1, wherein the therapeutic applicator positioning system comprises an ultrasound therapy applicator positioning system configured and arranged to support an ultrasound therapy applicator and to position the ultrasound therapy applicator in more than one degree of freedom.

10. The system of claim 1, wherein one of the anchors comprises a spring-loaded latch.

11. The system of claim 1, wherein the second platform is configured to be slidably positioned towards the head end or towards the foot end of the frame.

12. The system of claim 11, wherein the second platform includes a slot to slidably position the second platform with respect to the frame.

13. The system of claim 12, wherein a position of the second platform is lockable within the slot.

14. The system of claim 11, wherein the second platform is moveable along a rail on the frame, the rail parallel to a frame axis that extends from the head end to the foot end of the frame.

15. The system of claim 1, wherein the leg support and the foot support of each leg rest is disposed on a leg rest support stand.

16. The system of claim 15, wherein each leg rest support stand includes a knee support arm mechanically coupled to the leg support and a foot support arm mechanically coupled to the foot support.

17. The system of claim 16, wherein each leg rest support stand is slidably positionable along a leg rest positioning slot defined in a leg rest platform, the leg rest platform mounted on the frame.

18. The system of claim 1, wherein each leg rest includes a leg support pad and a foot support pad disposed on the leg support and the foot support, respectively.

19. A patient support system for supporting a patient during a thermal therapy procedure, the system comprising:
   a patient support platform, having a first end proximal to a patient's head and a second end proximal to a patient's feet, the support platform further configured and arranged to support at least a portion of a patient's upper body in a horizontal supine position;
   a pair of leg supports configured and arranged to support at least a portion of a patient's lower body or legs;
   a thermal therapy positioning rail including an elongated guide for slidably positioning an articulated thermal therapy applicator along an axis directed between said first end and said second end, and further configured and arranged to lockably secure said thermal therapy applicator in a determined position along said axis; and
   a cooling apparatus anchor point, mechanically fixing an articulated member at said anchor point on one end of the articulated member;
   a frame;
   a pair of leg rests, each leg rest comprising a respective one of the pair of leg supports and further comprising a respective foot support;
   wherein each of the leg supports and the foot support of each leg rest is disposed on a leg rest support stand;
   wherein each leg rest support stand includes a knee support arm mechanically coupled to the leg support and a foot support arm mechanically coupled to the foot support; and
   wherein each leg rest support stand is slidably positionable along a leg rest positioning slot defined in a leg rest platform, the leg rest platform mounted on the frame.

20. A system for supporting a patient, comprising:
   a frame having a head end and a foot end;
   a first platform mounted on the frame, the first platform configured to support the patient;
   a second platform mounted on the frame, the second platform disposed between the foot end of the frame and the first platform;
   a cooling device support that positions and releasably secures a cooling device, the cooling device support mounted on the second platform at a first attachment point;
   a therapeutic-applicator-positioning-system support configured and arranged to support and releasably secure a therapeutic applicator positioning system, the therapeutic-applicator-positioning-system support mounted on the second platform at a second attachment point, the second platform being lockable with respect to the frame to secure the therapeutic applicator positioning system at a desired position between the head end and the foot end of the frame; and a pair of leg rests, each leg rest comprising a leg support and a foot support, each leg rest being disposed on the frame and configured to be slidably positioned towards the head end or towards the foot end of the frame, wherein the system is constructed of a magnetic resonance imaging (MRI) compatible material suitable for use in an MRI environment during a medical procedure; and wherein the cooling device support is slidably positionable within a slot in the second platform, the slot extending parallel to a frame axis that extends from the head end to the foot end of the frame.

21. A system for supporting a patient, comprising:

a frame having a head end and a foot end;

a first platform mounted on the frame, the first platform configured to support the patient;

a second platform mounted on the frame, the second platform disposed between the foot end of the frame and the first platform;

a cooling device support that positions and releasably secures a cooling device, the cooling device support mounted on the second platform at a first attachment point;

a therapeutic-applicator-positioning-system support configured and arranged to support and releasably secure a therapeutic applicator positioning system, the therapeutic-applicator-positioning-system support mounted on the second platform at a second attachment point, the second platform being lockable with respect to the frame to secure the therapeutic applicator positioning system at a desired position between the head end and the foot end of the frame; and a pair of leg rests, each leg rest comprising a leg support and a foot support, each leg rest being disposed on the frame and configured to be slidably positioned towards the head end or towards the foot end of the frame, wherein the system is constructed of a magnetic resonance imaging (MRI) compatible material suitable for use in an MRI environment during a medical procedure;

wherein the leg support and the foot support of each leg rest is disposed on a leg rest support stand;

wherein each leg rest support stand includes a knee support arm mechanically coupled to the leg support and a foot support arm mechanically coupled to the foot support;

and wherein each leg rest support stand is slidably positionable along a leg rest positioning slot defined in a leg rest platform, the leg rest platform mounted on the frame.

* * * * *